United States Patent
Estes et al.

(10) Patent No.: US 6,613,089 B1
(45) Date of Patent: Sep. 2, 2003

(54) LATERALLY EXPANDING INTERVERTEBRAL FUSION DEVICE

(75) Inventors: Bradley T. Estes, Memphis, TN (US); Andrew M. Dickson, Gallatin, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/696,715

(22) Filed: Oct. 25, 2000

(51) Int. Cl.$^7$ .................................................. A61F 2/44
(52) U.S. Cl. ................................ 623/17.11; 623/11.11
(58) Field of Search .......................... 623/11.11, 17.11, 623/17.16, 16.11, 23.58

(56) References Cited

U.S. PATENT DOCUMENTS

| | | |
|---|---|---|
| 4,512,038 A | 4/1985 | Alexander et al. |
| 4,645,503 A | 2/1987 | Lin et al. |
| 4,945,127 A | 7/1990 | Kagawa et al. |
| 4,950,258 A | 8/1990 | Kawai et al. |
| 5,145,935 A | 9/1992 | Hayashi |
| 5,189,110 A | 2/1993 | Ikematu et al. |
| 5,192,326 A * | 3/1993 | Bao et al. ................. 623/17.11 |
| 5,534,028 A * | 7/1996 | Bao et al. ..................... 623/17 |
| 5,603,713 A | 2/1997 | Aust et al. |
| 5,603,722 A | 2/1997 | Phan et al. |
| 5,607,474 A | 3/1997 | Athanasion |
| 5,674,286 A * | 10/1997 | D'Alessio et al. ........ 623/11.11 |
| 5,676,699 A | 10/1997 | Gogolewski et al. |
| 5,716,410 A | 2/1998 | Wang et al. |
| 5,716,416 A | 2/1998 | Lin |
| 5,749,916 A | 5/1998 | Richelsoph |
| 5,824,093 A * | 10/1998 | Ray et al. ................. 623/17.11 |
| 5,868,745 A | 2/1999 | Alleyne |
| 5,868,746 A | 2/1999 | Sarver et al. |
| 5,919,234 A | 7/1999 | Lemperle et al. |
| 5,954,744 A | 9/1999 | Phan et al. |
| 5,976,186 A * | 11/1999 | Bao et al. ................. 623/17.11 |
| 6,017,366 A | 1/2000 | Berman |
| 6,019,793 A | 2/2000 | Perren et al. |

(List continued on next page.)

FOREIGN PATENT DOCUMENTS

| | | | |
|---|---|---|---|
| EP | 0326426 | 8/1989 | |
| EP | 1000958 | 5/2001 | |
| FR | 2712486 | 5/1995 | ............. A61F/2/44 |
| FR | 2 718 634 | 10/1995 | |
| WO | WO 97/09007 | 3/1997 | ............. A61F/2/06 |
| WO | WO 98/38918 | 9/1998 | ........... A61B/17/00 |
| WO | WO 00/44319 | 8/2000 | ............. A61F/2/44 |
| WO | WO 00/59412 | 10/2000 | ............. A61F/2/44 |
| WO | WO0025706 | 8/2001 | |

OTHER PUBLICATIONS

Blanchard, C.R., "Biomaterials: Body Parts of the Future," Technology Today, Fall 1995.

Middleton, J.C., Tipton, A.J., "Synthetic Biodegradable Polymers as Medical Devices," Medical Plastics and Biomaterials Magazine, Mar. 1998.

*Primary Examiner*—Kevin Shaver
*Assistant Examiner*—Michael B. Priddy
(74) *Attorney, Agent, or Firm*—Woodard, Emhardt, Moriarty, McNett & Henry LLP

(57) ABSTRACT

This invention relates to intervertebral spacers for use in orthopedic treatment of spinal defects. The intervertebral space is formed of a shape memory polymer. The spacer can be fabricated into a desired configuration and then deformed into an alternative or deformed configuration. Cooling the deformed spacer effectively freezes the spacer into its deformed conformation. The deformed configuration can be selected to facilitate implantation of the spacer into a prepared disc space between adjacent vertebrae. During operation, the surgeon can heat the spacer to allow it to revert to its original configuration. The spacer in its original conformation is sized to restore and/or maintain the adjacent vertebrae in a desired conformation and disc space height.

26 Claims, 7 Drawing Sheets

U.S. PATENT DOCUMENTS

| | | | |
|---|---|---|---|
| 6,022,352 A | 2/2000 | Vandewalle | |
| 6,024,764 A | 2/2000 | Schroeppel | |
| 6,039,761 A | 3/2000 | Li et al. | |
| 6,045,579 A | 4/2000 | Hochshuler et al. | |
| 6,071,982 A | 6/2000 | Wise et al. | |
| 6,090,996 A | 7/2000 | Li | |
| 6,093,205 A | 7/2000 | McLeod et al. | |
| 6,102,932 A * | 8/2000 | Kurz | 606/200 |
| 6,102,933 A | 8/2000 | Lee et al. | |
| 6,127,597 A | 10/2000 | Beyar et al. | |
| 6,132,465 A * | 10/2000 | Ray et al. | 623/17.16 |
| 6,136,031 A | 10/2000 | Middleton | |
| 6,156,842 A | 12/2000 | Hoenig et al. | |
| 6,160,084 A * | 12/2000 | Langer et al. | 528/272 |
| 6,193,757 B1 * | 2/2001 | Foley et al. | 623/17.16 |
| 6,206,883 B1 | 3/2001 | Tunc | |
| 6,221,075 B1 | 4/2001 | Tormala et al. | |
| 6,264,695 B1 * | 7/2001 | Stoy | 623/17.16 |
| 6,281,262 B1 * | 8/2001 | Shikinami | 523/105 |
| 2003/0055198 A1 * | 3/2003 | Langer et al. | 528/80 |

* cited by examiner

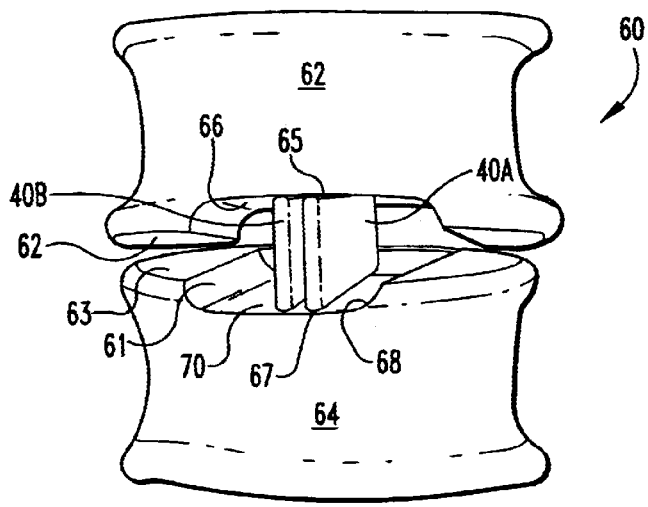
Fig. 4
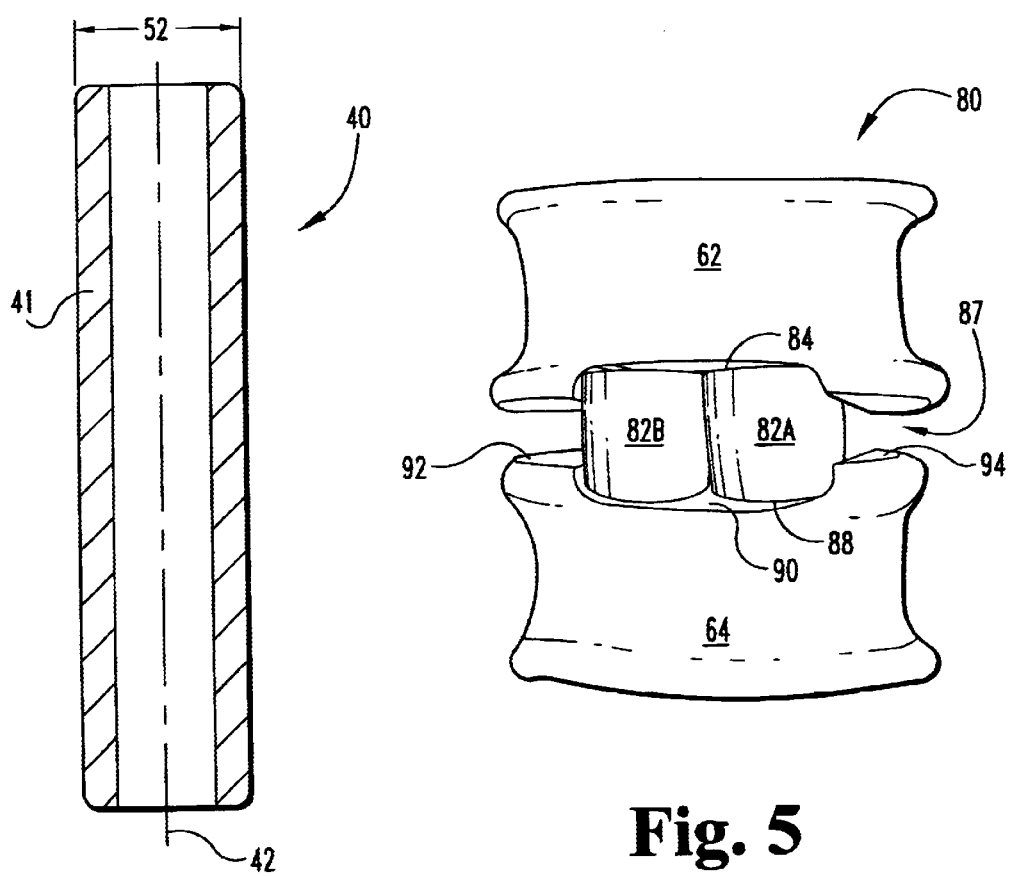
Fig. 3
Fig. 5

LATERALLY EXPANDING INTERVERTEBRAL FUSION DEVICE

BACKGROUND OF THE INVENTION

In general, this invention relates to intervertebral spacers and their use in orthopedic treatment. More specifically, the present invention is directed to intervertebral spacers composed of a shape memory polymeric material. The intervertebral spacers can be deformed and induced to recover their original configuration as desired to facilitate orthopedic treatment of spinal defects.

Removal of damaged or diseased discs and implantation of intervertebral spacers into the disc space are known medical procedures used to restore disc space height, and to treat chronic back pain and other ailments. The spacers can be formed of a variety of materials—both resorbable and non-resorbable materials—including bone-derived material, metallic, ceramic, and polymeric materials. Typically, spacers are pre-formed into a general configuration that is easy to fabricate or, in selected examples, spacers are pre-formed to a generalized configuration that resembles idealized vertebral endplates. During surgery, the vertebral endplates must be prepared to receive the spacers. This typically involves either partial or full discectomy to remove the damaged or diseased disc. Thereafter the bone tissue of the vertebral endplates is cut in preparation to receive the spacer. It is also desirable to promote fusion between the vertebral bodies that are adjacent to the damaged or diseased discs. The endplates are often shaved, exposing the cancellous bone tissue in the vertebral body, to enhance the fusion between the vertebrae. Additionally, an osteogenic material is combined with a spacer—typically packed inside the spacer body and in the disc space around the space—to further promote bone growth. Current surgical techniques approach the disc space from a variety of directions, including anteriorly, posteriorly, posterior-laterally and anterior-laterally. Regardless of the direction of approach, the surgery is extremely difficult, and several organs, vessels and nerve structures must be avoided. From the posterior approach, surgeons must be very careful to avoid the spinal cord and associated nerves. An oblique approach, such as from a posterior lateral or anterior lateral direction, offers many advantages. However, the oblique approaches only afford access to one side of the disc space. Obviously, it is desirable to avoid multiple incisions into the patient. Further smaller incisions and narrow passageways into the targeted disc space decrease the patients post surgical pain and recovery time. Further complicating the situation, the exposed cancellous bone tissue central to the vertebral body is spongy and an implanted spacer can subside into the tissue.

Therefore, it would be desirable to provide a spacer capable of withstanding the biomechanical loads exerted by the spinal column without subsiding into the spongy cancellous bone tissue. The spacer should also bear against strong cortical bone around the periphery of the endplates. Yet the space should be capable of being inserted into the disc space via a minimally invasive route.

Thus, in view of the above-described problems, there continues to be a need for advancement in the relevant field, including spacers for treatment of spinal defects and methods of treating spinal defects. The present invention is such an advancement and provides a wide variety of additional benefits and advantages.

SUMMARY OF THE INVENTION

The present invention relates to intervertebral spacers, the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In general, this invention provides an expandable spacer for implantation between adjacent vertebrae to treat spinal defects. The spacer can be formed of a shape member polymer (SMP) and molded into a pre-selected configuration. Fabrication of the spacer using a shape memory polymeric material imparts novel and particularly advantageous characteristics to the intervertebral space. In a preferred embodiment, the spacer fabricated from a SMP can be molded into a desired configuration. However, when the spacer body is heated above a deformation temperature ($T_d$)—which is usually equivalent to the glass transition temperature ($T_g$) of the polymeric material, the polymeric material becomes elastic. When heated to a temperature equal to or above $T_d$, the spacer body can be deformed to a wide variety of configurations by applying pressure or forcing it into a mold. The spacer body can be "frozen" into the deformed configuration by cooling it below the $T_d$ while the body is maintained in the deformed configuration. Thereafter the deformed spacer body retains the deformed configuration until it is heated above $T_d$. When the spacer body is reheated above $T_d$, the SMP again becomes elastic; and in the absence of any applied pressure, the spacer body automatically reverts to its original molded configuration. This process can be repeated any number of times without detrimental effect on the SMP or the spacer itself.

In one form, the present invention provides a fabricated. intervertebral spacer molded to a desired shape and/or size. The spacer comprises a body composed of a polymeric material that exhibits a shape memory defect above a deformation temperature. Above the deformation temperature, the body can be deformed to a first configuration. Preferably, the first configuration provides a reduced external volume or cross-sectional area. Cooling the deformed spacer to a temperature below the deformation temperature effectively freezes the spacer body in the first configuration. The deformed spacer can then maintain the first configuration until it is desired to cause the body to revert to its original, molded configuration. It should be understood that a spacer can be deformed/conformed to a desired configuration and/or allowed to recover to its original configuration at any time—either before or after implantation into the disc space. Since the deformed spacer can be smaller than the molded spacer, the deformed spacer can be more readily inserted into the disc space. In a particularly preferred form, after implantation the deformed spacer is heated above its deformation temperature, which permits and allows it to revert to its original configuration or a second configuration substantially equivalent to the original configuration. The resulting implanted spacer can essentially fill the disc space, if desired, while only requiring a small entrance incision.

In one form the present invention provides an intervertebral spacer for implantation into a disc space between adjacent vertebrae. The spacer comprises a deformable body formed to include a shape memory polymeric material. The body comprises a first bearing surface, an opposite second bearing surface, and a peripheral sidewall positioned therebetween. The body has a lateral axis extending therethrough and positioned to lie substantially parallel the first bearing surface. The body deforms in a direction along said lateral axis upon application of selected stimuli. In one preferred embodiment, after the spacer is implanted into a disc space, the body expands laterally in the disc space. In other preferred embodiments, the selected stimuli include heating the body to a temperature equal to or greater than about 38° C.

In another form, the present invention provides a spacer for insertion into the spine. The spacer is formed of a material comprising a shape memory polymer and provided in an original configuration and deformable to a second configuration, wherein the spacer reverts to the original configuration by action of the shape memory polymer.

In yet another form, the present invention provides a method of orthopedic treatment. The method comprises: preparing a disc space between adjacent vertebrae to receive an intervertebral spacer and implanting an intervertebral spacer in the prepared disc space. The spacer comprises a deformable body composed of a shape memory polymeric material and has a first bearing surface adapted to bear against a vertebral endplate. The body is provided in a first configuration and defines a lateral axis that is positioned to lie substantially parallel to the first bearing surface. The spacer is subjected to a selected stimulus and deforms along the longitudinal axis to a second configuration.

It is one object of the present invention to provide an expanding intervertebral spacer for use in orthopedic treatment.

Further objects, features, aspects, forms, advantages and benefits shall become apparent from the description and drawings contained herein.

BRIEF DESCRIPTION OF THE DRAWINGS

FIG. 3 is a side elevation view in full section of the deformed spacer of FIG. 2.

FIG. 4 is a side elevation view illustrating the bi-lateral placement of a pair of deformed spacers according to FIG. 2 implanted in a prepared disc space between adjacent vertebrae.

FIG. 5 is a side elevation view illustrating a pair of expanded spacers derived from the spacers of FIG. 4.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

In general, this invention provides an expandable spacer for implantation between adjacent vertebrae to treat spinal defects. The spacer can be formed of a shape memory polymer (SMP) material and fabricated to a pre-selected, original configuration. The spacer can be heated to a deformation temperature ($T_d$) and deformed into a first configuration, for example, a collapsed state exhibiting a reduced cross-sectional profile. The deformed spacer can be readily implanted into the disc space through a small incision and a narrow passageway using either laparoscopic, endoscopic or other minimally invasive techniques. In a preferred form, after the deformed implant is received within the disc space, the spacer can be subjected to a pre-selected stimulus and expanded to a second confirmation that is substantially equivalent to the original confirmation. In a particularly preferred embodiment, the expanded spacer extends laterally across the disc space, substantially filling the disc space. In other forms, the molded spacer can be deformed into a first configuration selected to conform to targeted bone defect. Thereafter the spacer can be heated to a deformation temperature or above and allowed to recover to its original configuration. The process can be repeated as desired until the desired configuration is achieved. Additionally, the original, fabricated spacer can be provided in a variety of preselected original shapes and sizes with additional external/internal structures. The resulting implanted spacers are sized to maintain the desired disc space height between the different vertebral bodies, including cervical, thoracic, lumbar, and sacral vertebral bodies. In other forms, the spacer includes a cavity to serve as a depot for osteogenic material and promote spinal fusion of the adjacent vertebral bodies. In still yet other forms, the spacer can be inserted into the disc space or a vertebral body (vertebroplasty procedure) to treat orthopedic diseases such as osteoporosis.

Figure 1:
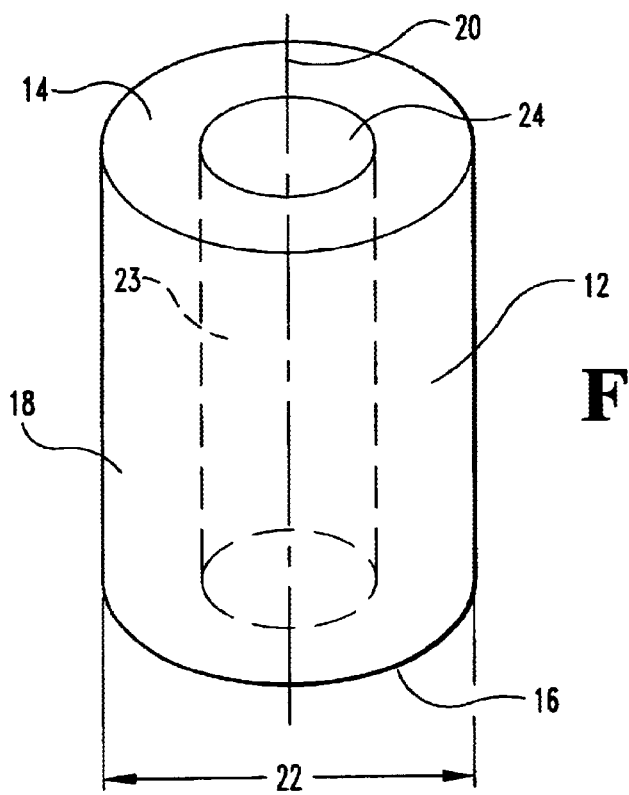
FIG. 1 is a perspective view of one embodiment of a molded spacer for use in the present invention.

FIG. 1 is an illustration of one embodiment of a molded spacer 10 for use in the present invention. Molded spacer 10 includes a body 12 formed of a shape memory polymeric material. Body 12 includes an upper, first surface 14 and an opposite second surface 16. A peripheral sidewall 18 separates first surface 14 from second surface 16. First and second surfaces are provided to bear against opposing endplates of adjacent vertebrae. While both first and second surfaces, 14 and 16, are illustrated as substantially planar surfaces, one or both of these surfaces can be provided in alternative forms. Preferably the alternative forms conform to the anatomical configuration of to the endplates of the respective vertebrae—whether naturally occurring or in an altered form either surgically or by trauma and/or disease. For example, first surface 14 can be molded to exhibit a convex profile. Alternatively, first surface 14 can be molded to resemble only a portion of the respective, opposing endplate. In this regard, a pair of spacers 10 each resembling the mirror image of the other, can be implanted together into the disc space. (See, for example, FIGS. 4 and 5, which depict the bi-lateral placement of a pair of spaces.) In the illustrated embodiment, body 12 is illustrated as a cylinder concentric about vertical axis 20. Peripheral sidewall 18 is illustrated as a continuous, curved wall encircling body 12. As will be seen in alternative embodiments described below, the peripheral sidewall can include various wall portions, each having it own surface features. Body 12 has a diameter or lateral dimension ($L_1$), measured orthogonal to axis 20 and defined by reference line 22. Lateral dimension $L_1$ can vary, depending upon the level in the spinal column in which spacer 10 is implanted and whether the vertebrae adjacent to the targeted disc space are cervical, thoracic, lumbar, or sacral vertebrae. The lateral dimension can be selected to stabilize spacer 10 in the disc space and provide adequate support for the spinal column. Lateral dimension can be selected to inhibit subsidence of the implanted spacer into cancellous bone tissue. Preferably, the lateral dimension is selected so that at least a portion of first surface 14 and second surface 16 bear against the thick cortical bone tissue in the apophyseal ring of the vertebrae and/or internal of the cortical rim of the vertebrae. In preferred embodiments, $L_1$ can be selected to be between about 6 mm and about 50 mm; more preferably, between about 10 mm and about 16 mm. Preferably, two implants would be placed in the disc space. However, one large implant in the 50 mm range could be placed.

The height of body 12 can be selected to maintain the desired disc space height between the selected vertebrae. Thus, the height of body 10 can vary, depending on whether spacer 12 is inserted between cervical, thoracic, lumbar, and/or sacral vertebrae. The height of body 12 measured along vertical axis 20 can be selected to be between about 3 mm and about 20 mm; more preferably, between about 4 mm and about 14 mm.

Body 12 also includes an interior cavity 23 for receipt of osteogenic material to promote spinal fusion between adjacent vertebrae. At least one opening 24 extends into the interior cavity. Preferably, at least one opening extends through both bearing surfaces 14 and 16. Additionally, an opening can extend through peripheral sidewall 18 into cavity 22. The opening through peripheral sidewall 18 permits introduction of an osteogenic material into cavity 23 after spacer 12 has been inserted into the disc space.

Figure 2:
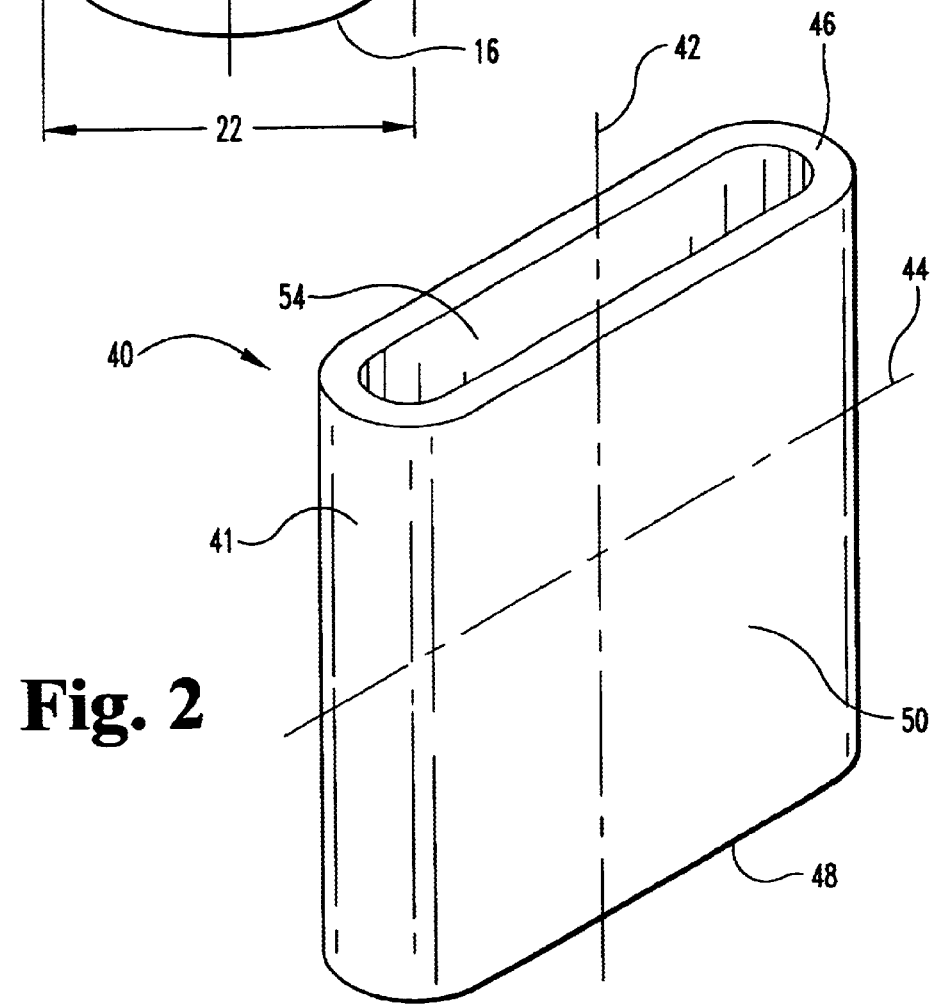
FIG. 2 is a perspective view of one embodiment of a deformed spacer for use in the present invention.

FIGS. 2 and 3 illustrate one embodiment of a deformed spacer 40 comprising a deformable body 41 according to the present invention. Deformed spacer 40 is derived from molded spacer 10 by heating the selected spacer above a different deformation temperature ($T_d$) and then exerting force to deform spacer 12 into a desired, first configuration. Deformed spacer 40, similar to molded spacer 10, includes first bearing surface 46, an opposite second bearing surface 48, and a peripheral sidewall 50 positioned therebetween. Body 41 includes an internal cavity 54 provided for receipt of an osteogenic material. In the illustrated embodiment, deformed spacer 40 is provided as a substantially elongated spacer having a longitudinal axis 44. Thus, spacer 40 can be derived from molded spacer 10 by heating spacer 10 above a deformation temperature and applying an external force substantially orthogonal to vertical axis 20, resulting in the collapse of peripheral sidewall 18 into interior cavity 23.

As can be observed from FIG. 3, the deformed spacer presents a substantially reduced cross-sectional profile compared to spacer 10 when viewed from a direction substantially parallel to vertical axis 42. This is indicated by the smaller longitudinal dimension ($L_2$) illustrated by reference line 52. In preferred embodiments, longitudinal dimension $L_2$, measured orthogonal to axis 42 and represented by reference line 52, is about 50% shorter than the longitudinal distance $L_1$ of spacer 12. More preferably, $L_2$ is at least about 60% shorter than $L_1$; still more preferably, at least about 70% shorter than $L_1$.

While in the illustrated embodiment spacer 40 is provided as a substantially flat cylinder, it should be understood by those skilled in the art that a deformed spacer can be prepared having a wide variety of configurations, which provide reduced cross-sectional area. For example, a deformed spacer can be provided by compressing, folding and/or collapsing the peripheral sidewall onto itself to yield a deformed spacer resembling an accordion or pleated structure. (See, for example, FIG. 8.) Additionally, a deformed spacer can be provided by first compressing a molded spacer into a flattened configuration and thereafter rolling the spacer to provide a spirally wound cylinder having a substantially reduced cross-sectional area. Examples of spirally wound orthopedic implants are disclosed in a co-pending U.S. patent application Ser. No. 09/696,389 and entitled "Self-Forming Orthopedic Implants" filed on Oct. 25, 2000, which is incorporated herein by reference in its entirety. Upon heating to a temperature above the deformation temperature or above, the spirally wound deformed spacer can then unwind and then further fully expand into its original configuration.

The deformation temperature can be pre-selected as is described more fully below. In preferred embodiments, the deformation temperature is selected to be above body temperature (about 37° C.), but less than a temperature at which adjacent tissue (and neighboring organs) can become substantially traumatized and damaged. In preferred embodiments, the deformation temperature ($T_d$) is selected to be above 38° C. and below about 100° C.; more preferably, the deformation temperature is selected to be between about 38° C. and about 65° C.; still yet more preferably, the deformation temperature is selected to be between about 38° C. and about 45° C. While the foregoing discussion has focused on selecting an SMP that exhibits an elasticity or super high elasticity above a selected temperature, it should be understood that other polymers can be selected for this invention that respond to other stimuli, such as light or radiation, pH changes and/or chemical and solvent additives.

FIG. 4 illustrates the bi-lateral placement of a pair of spacers 40 of FIGS. 2 and 3 between adjacent vertebrae 62 and 64. It can readily be seen from the illustrated embodiment that the longitudinal width of either spacer 40A or 40B is substantially smaller than the longitudinal width of the prepared disc space 61. In this illustrated embodiment, spacers 40A and 40B have been inserted through an anterior approach. It is considered to be within the scope of the present invention to insert the spacers disclosed herein through any approach, for example, through a posterior approach, a posterior-lateral approach, and/or an anterior-lateral approach. It should be understood that by inserting spacers 40A and 40B through the various approaches, the longitudinal axis 44 of the respective spacers may be positioned to lie in substantial alignment with the direction of approach. Regardless of the direction of approach, subjecting the implanted spacers to a selected stimulus allows the spacers to expand primarily laterally thorough the disc space and, in a preferred embodiment, substantially fill the prepared disc space.

Preferably, implantation of either 40A or 40B requires only minimally invasive surgical techniques. Primarily, implants 40A and 40B can be inserted through a primary incision and through a working channel extending down to the targeted disc space. Implantation of a laterally expandable spacer provides distinct advantages when the targeted disc space is approached from an oblique angle such as a posterior-lateral or an anterior-lateral direction. Obviously, it is desirable to use a single incision during the operation. However, a single incision makes it difficult for the surgeon to introduce a spacer to the distal side of the disc space. A laterally expanding spacer can obviate the need to place a separate spacer proximal to the distal side of the disc space. In preferred forms, a single laterally expanding spacer can be introduced into the disc space and then expanded in vitro to extend laterally across the disc space from the proximal cortical rim to the distal cortical rim.

Implants such as 40A and 40B can be inserted into the intervertebral space 61 such that upper bearing surface 64 bears against the endplate 66 of vertebrae 62 and lower bearing surface 68 bears against vertebral endplate 70 of vertebrae 64. As can be seen from the illustrated embodiment, spacers 40A/B reside within a prepared disc space 61. Prepared disc space has been achieved by shaving portions of the cortical endplates 66 and 68, respectively, to expose the cancellous bone tissue composed of a spongy tissue that is found in the central portion of the respective endplates. While cancellous bone tissue is extremely effective for promoting bone fusion between the adjacent vertebrae, cancellous tissue does not provide sufficient structural strength to withstand the loads exerted by the spinal column. Therefore, it is preferable to provide spacers that bear against the hard, cortical bone tissue that can be found around the apophyseal ring around the perimeter of the endplates. The present invention provides spacers that can be inserted into a prepared disc space, using minimally invasive surgical techniques, and expanded to provide surfaces to bear against the cortical bone tissue and maintain intimate contact of any included osteogenic material with the cancellous bone tissue.

Referring specifically to FIG. 5, there is illustrated expanded spacers 82A and 82B in accordance with the present invention. Spacers 82A and 82B are derived from spacers 40A and 40B of FIG. 4. Spacer 82A will be discussed in more detail with the understanding that the same discussion applies equally to spacer 82B. It can be clearly illustrated in the figure that the longitudinal dimension of spacer 82A is substantially greater than that exhibited by spacer 40A.

In a preferred embodiment, expanded spacer 40A reverts to the substantially equivalent configuration of that exhibited by the original spacer 10. However, it will be understood that because of boundary constraints within the disc space 81, spacer 82A may not expand to the height and/or width of the original configuration. Instead, spacer 82A may expand to a height and/or width to the extent allowed by structures within and surrounding the disc space, such as the cortical rim surrounding the vertebral bodies and the endplates. When spacer 82A is maintained at the deformation temperature or above, the SMP material exhibits an elasticity or super elasticity, and it can be compressed by any number of forces. Thus, the compressive force exerted by the opposing endplates of vertebrae 62 and 64 can compress upon the respective first bearing surface 84 and opposing second bearing surface 88 to conform these bearing surfaces to the existing anatomical structure of the opposing endplates. Thus, while it may be observed that spacer 82A expands in a direction laterally within the intervertebral space 81, it will also be understood by those skilled in the art that compression forces exerted by the adjacent vertebrae may at the same time compress first and second bearing surfaces 84 and 88 to provide a spacer 82 having a reduced height of that compared to the original, molded spacer 10. Typically during surgery, the vertebrae are distracted to increase the disc space height. The amount of distraction can be varied and controlled by the surgeon. The resulting spacer 82 can be formed to matingly engage respective endplates. This provides an optimal fit in the disc space, decreases the potential for retropulsion of the implanted spacer, and when the spacer is packed with osteogenic material, maintains the osteogenic material in intimate contact with the cancellous bone tissue.

Once spacer 82A is cooled below the deformation temperature, spacer 82A is then frozen into a substantially rigid form that does not further decompress or expand when stressed by the load exerted by the spinal column. In one form, the SMP material is selected to exhibit a compressive modulus similar to that of cancellous bone tissue. Preferably, the SMP material selected for spacer 82A below its deformation temperature exhibits a compression modulus between about 2 MPa and about 30 MPa; more preferably between about 8 MPa and about 15 MPa. As discussed more fully below, the shape memory polymeric material can be selected from a wide variety of known materials, and it can include both biodegradable and non-biodegradable materials. While the foregoing discussion has been applied to a pair of identical spacers 82A and 82B, use of two or more unique spacers within the same intervertebral space is also included with this invention. For certain orthopedic treatments, it may be desirable to use two different, unique spacers. In one embodiment, the two spacers can be mirror images of each other. Accordingly, each of the spacers can be provided in a configuration that matingly bears against only a portion of the opposing endplates. For example, a single spacer may be used to bear against a portion of the endplate beginning at the midline of the endplate and extending laterally toward the lateral facet. Alternatively, because of a bone defect, tumor, or diseased bone tissue, the surgeon may desire to combine in a selected vertebral space differently sized spacers or even spacers with a different configuration. (See, for example, the exemplary embodiments and spacers discussed below and illustrated in FIGS. 6–8.)

Figure 6:
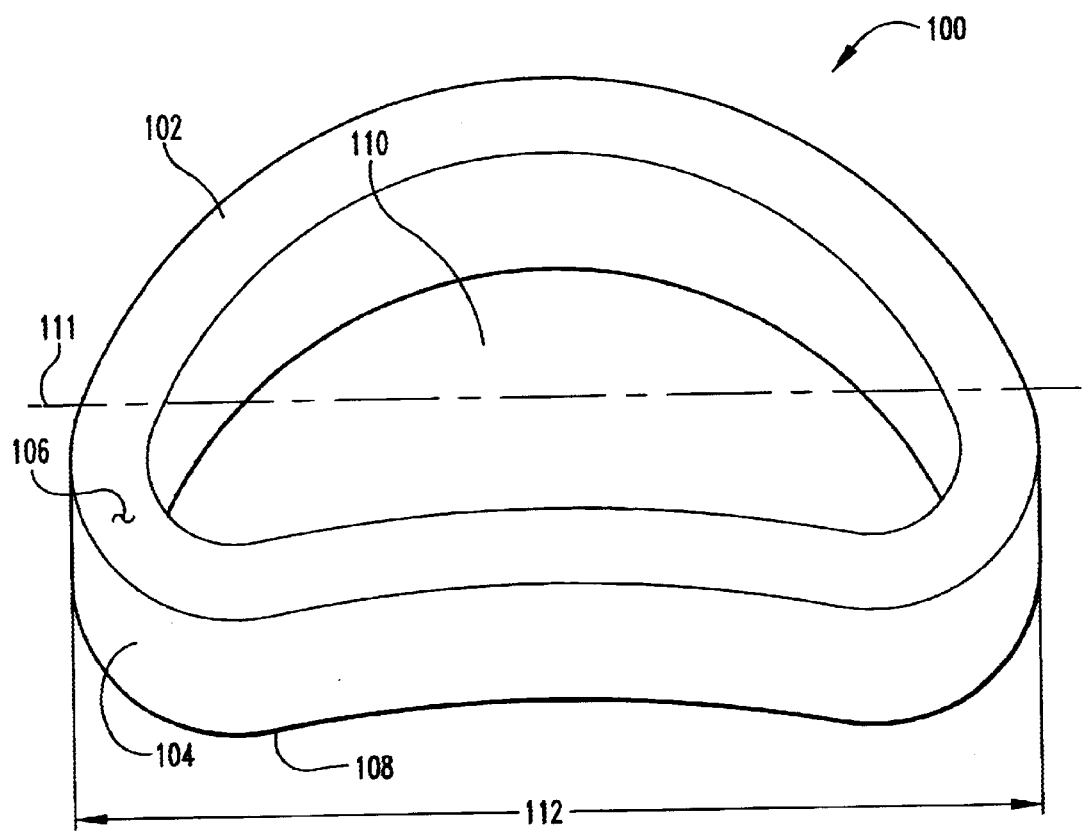
FIG. 6 is a perspective view of an alternative embodiment of a molded spacer for use in the present invention.

FIG. 6 illustrates an alternative embodiment for a molded spacer 100 in accordance with the present invention. Spacer 100 includes body 102. Body 102 provides a footprint that resembles the endplate of a lumbar vertebra. Alternatively, it can be described as a kidney-shaped body 102. Body 102 further includes a first bearing surface 106, an opposite second bearing surface 108, and a peripheral sidewall 104 extending therebetween. In one direction, body 102 has a length ($L_3$) measured along lateral axis 111 illustrated by reference line 112. Preferably, $L_3$ is selected so body 102 substantially fills the disc space. Cavity 110 is provided internally of body 102. Cavity 110 serves a depot for osteogenic material to facilitate bone fusion between the adjacent vertebrae. Spacer 100 can be formed of an SMP material substantially as has been described for spacer 10. To facilitate the addition of an osteogenic material into cavity 110, sidewall 104 can include at least one opening (not shown), which can be provided in any number of sizes and locations about peripheral sidewall 104.

Figure 7:
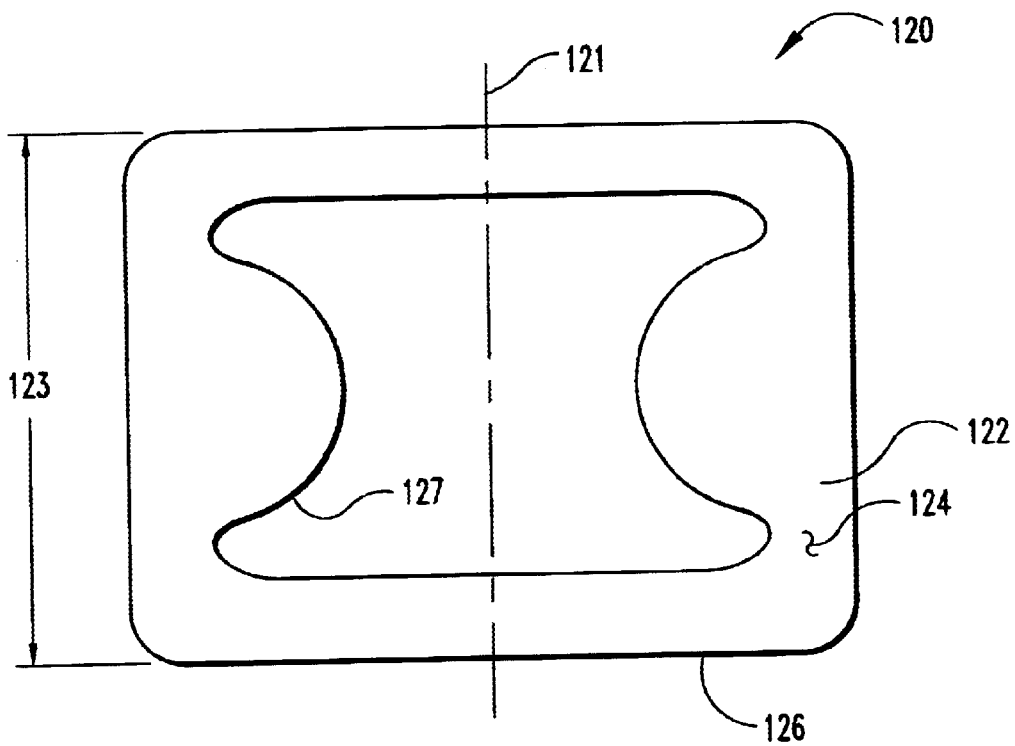
FIG. 7 is a top plan view of a deformed space derived from the molded spacer of FIG. 6.

FIG. 7 illustrates a deformed spacer 120 derived from compressing spacer 100 along lateral axis 109. Spacer 120 includes body 122 having a first bearing surface 124 and a peripheral sidewall 126. Peripheral sidewall 126 includes an interior wall surface 127. It can be seen from the illustrated embodiment that in comparison with spacer 100, internal wall surface 127 collapses back on itself upon compression of spacer 100 along lateral axis 121. Further, it can be observed from the illustration that spacer 120 has a lateral dimension ($L_3$) illustrated by reference line 123 that is substantially shorter than the counterpart lateral dimension illustrated by reference line 112 of spacer 100.

In preferred embodiments, deformed spacer 120 is formed by heating spacer 100 to a temperature equal to or greater than a deformation temperature and constraining body 100 in a mold while at the same time applying compressive force along lateral axis 109. In this fashion, compression of the spacer does not result in expansion of the spacer in a direction orthogonal to axis 111.

Figure 8:
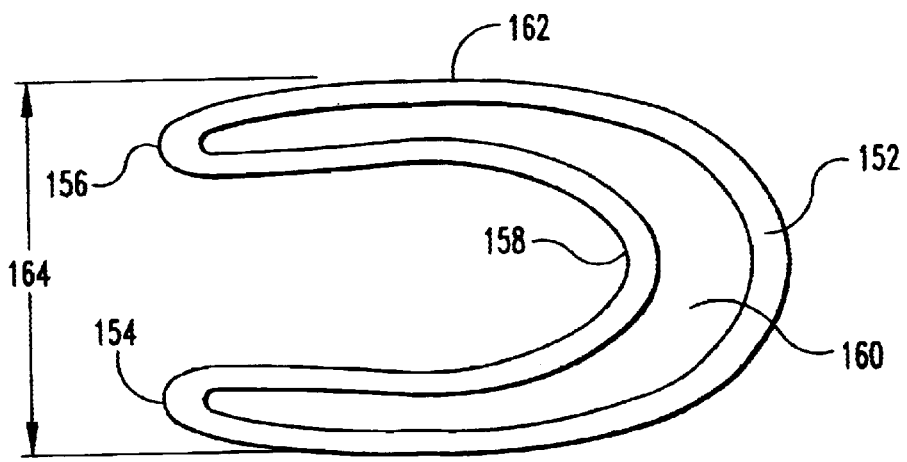
FIG. 8 is a top plan view of an alternative embodiment of a deformed spacer derived from the molded spacer of FIG. 6.

FIG. 8 illustrates another embodiment of a deformed spacer 150 derived from molded spacer 100. Spacer 150 can be prepared by heating spacer 100 to a temperature equal to or greater than a deformation temperature and applying a compression force along axis 111 as well as applying a compressive force orthogonal to lateral axis 111. Peripheral sidewall 152 collapses back upon itself and creates at least one, preferably two or more, folded wall portions 154, 156 and, optionally, 158; an internal wall portion 161; and an external wall portion 162. In this embodiment, it can readily be seen that interior cavity 160 is substantially reduced from cavity 110 for spacer 100. Furthermore, the lateral dimension of spacer 150 illustrated by reference line 164 is substantially smaller than that illustrated by reference line 112 for spacer 100.

Figure 9:
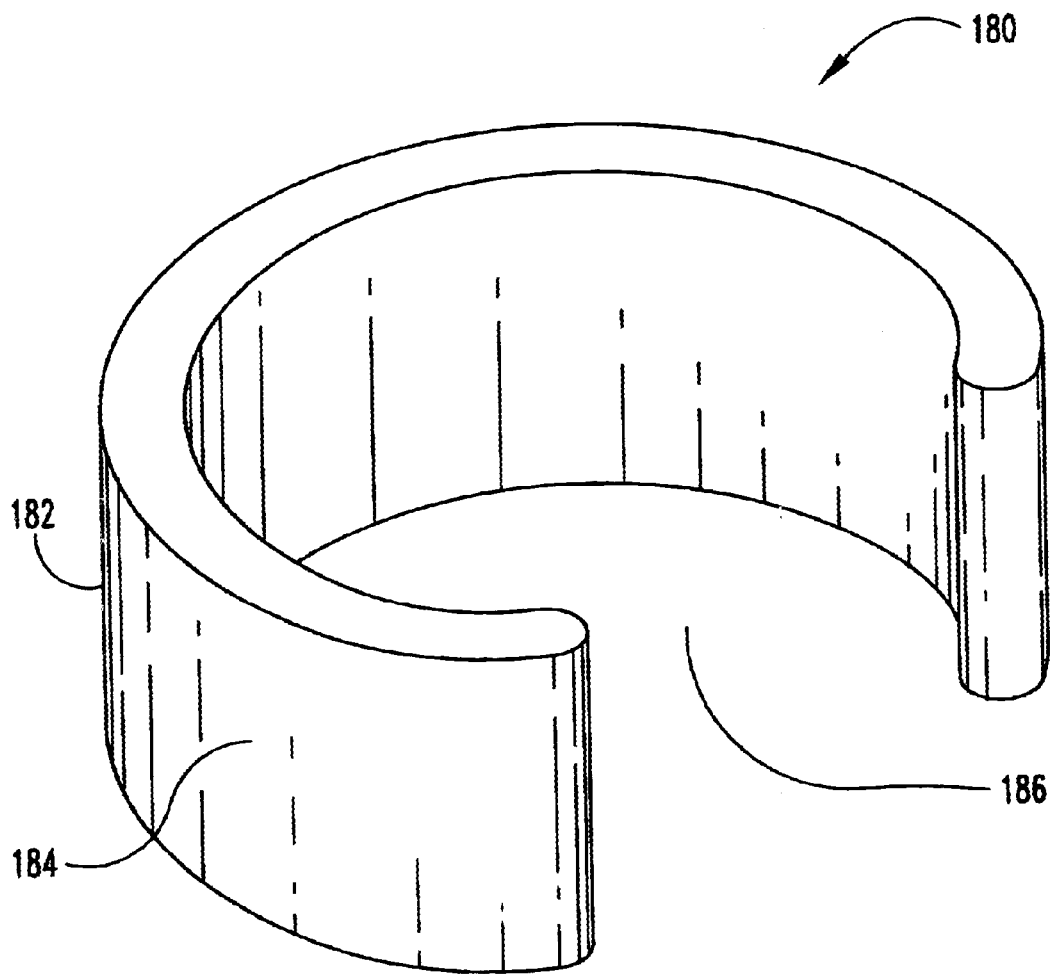
FIG. 9 is a perspective view of one embodiment of a fabricated "C" shaped spacer for use in the present invention.

FIG. 9 illustrates yet another embodiment of a curved spacer 180 for use in this invention. Spacer 180 defines a body 182 formed of a shape memory polymeric material and fabricated in an original configuration resembling a "C"shaped body. Sidewall 184 includes a cavity 186. Heating spacer 180 to a temperature greater than or equal to a deformation temperature allows body 182 to be deformed in a wide variety of configurations. Examples of curved shaped spacers are disclosed in co-pending U.S. patent application Ser. No. 09/696,146, and entitled "Vertically Expanding Intervertebral Body Fusion Devices" filed on Oct. 25, 2000, which is incorporated herein by reference in its entirety.

Figure 10:
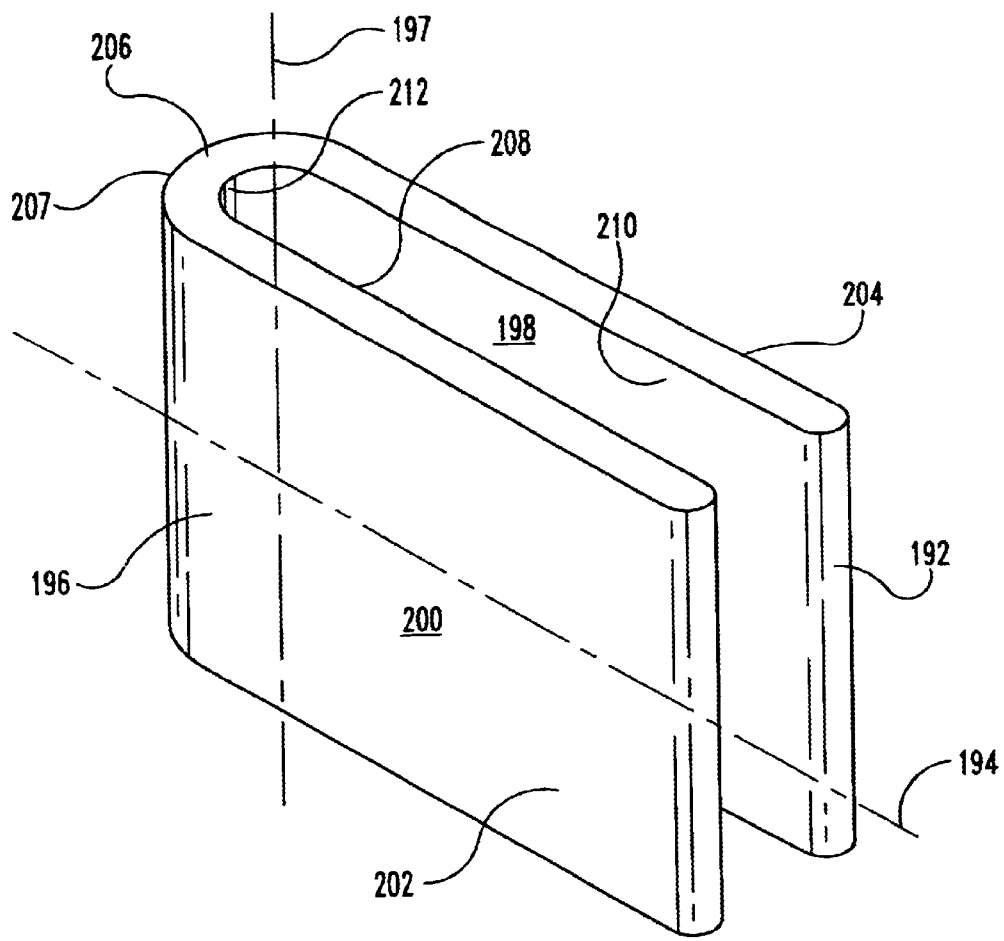
FIG. 10 is a perspective view of one embodiment of a deformed spacer derived from the spacer of FIG. 9.
Figure 11:
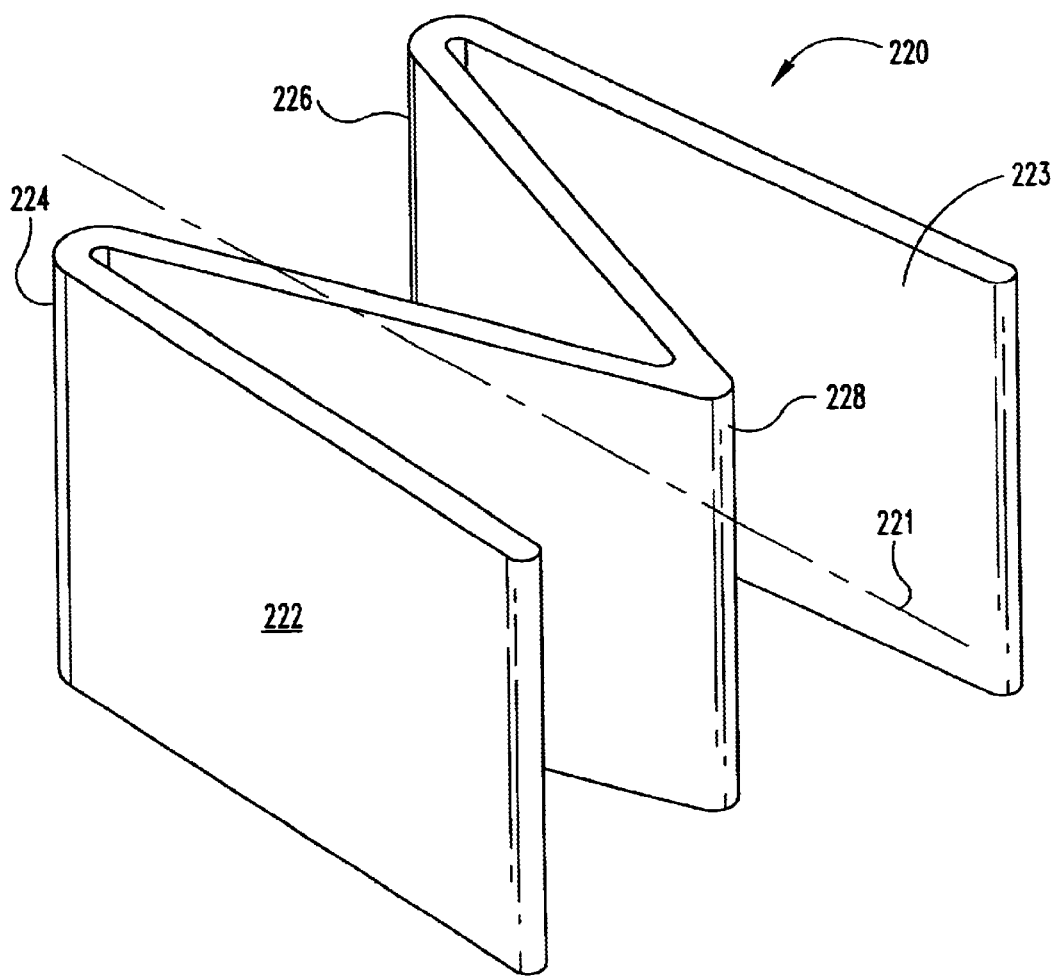
FIG. 11 is a top plan view of an alternative embodiment of a deformed spacer derived from the spacer of FIG. 9.

FIGS. 10 and 11 illustrate deformed spacers 190 and 220, respectively. Each deformed spacer 190 and 220 is derived from spacer 180. Spacer 190 comprises an elongate deformed body 192 defining a longitudinal axis 194. Sidewall 196 extends about the periphery of body 192. Sidewall 196 is folded along fold line 197 in a direction substantially orthogonal to longitudinal axis 194, resulting in the collapse and/or overlay of sidewall 196 back on to itself. This provides sidewall 196 with a plurality of internal surface portions 198 and external surface portions 200. In the illustrated embodiment, external surface portions 200 include a first exterior surface portion 202, an opposite exterior surface portion 204 and junction 206 therebetween. Junction 206 can be provided with a curved surface presenting a curved or streamlined end 207 to deformed spacer 190. Internal surface portions include a first internal surface 208, an opposing second internal surface 210, joined to surface 208 via interior corner 212. In one form, first interior surface 208 is spaced from second interior surface 210. In other embodiments, first interior surface bears against at least a portion of second interior surface 210.

Referring specifically to FIG. 11, there is illustrated an alternative embodiment of a deformed spacer 220. Deformed spacer 220 includes collapsed body 223 folded, creased or hinged like an accordion. Body 223 defines longitudinal axis 221 and a sidewall 222 folded along a plurality of fold lines. In the illustrated embodiment, sidewall includes external fold edges 224 and 226 and at least one internal fold edge 228.

It is to be understood that spacers 190 and 220 illustrate generalized configuration of deformed spacers for use in the present invention and that the exact conformation of a deformed spacer can vary greatly depending upon the direction and amount of force used to deform an original fabricated spacer. In use, both deformed spacers 190 and 220 can be implanted into a prepared disc space as has been described above for implants 42, 120 and 150.

The deformed spacers of the present invention can be inserted into a disc space using minimally invasive techniques. Preferably the minimally invasive techniques require and provide for using techniques formerly associated with endoscopic, laparoscopic, or other minimally invasive surgery techniques. Furthermore, the spacers of the present invention can be inserted into the disc space from a wide variety of approaches, including anteriorly, posteriorly, posterior-laterally or anterior-laterally. In other forms, the spacers of the present invention can be inserted using a guide tube commonly used in PLIF and ALIF surgical techniques. Such guide tubes are well-known to those skilled in the art.

It can be readily observed that when the deformed spacers are inserted into the prepared disc space, the spacer may not necessarily be constrained within the disc space. Therefore, the deformed spacer can be readily positioned and/or re-positioned during surgery to provide optimum efficacy and support. If necessary, the deformed spacer can be secured in a desired position using either temporary or permanent fasteners (not shown), which are commonly used for surgical techniques.

Each of the spacers discussed above can be formed of a material that comprises a shape memory polymer. The shape memory polymeric material can be selected from a wide variety of polymers, including biodegradable and non-biodegradable polymers. In preferred embodiments, the shape memory polymeric material is formed from oligomers, homopolymers, copolymers, and polymer blends that include polymerized monomers derived from 1, d, or d/l lactide (lactic acid); glycolide (glycolic acid); ethers; olefins, such as ethylene, propylene, butene-1, pentene-1, hexene-1, 4-methylpentene-1, styrene, norbornene and the like; butadiene; polyfunctional monomers such as acrylate, methacrylate, methyl methacrylate; esters, for example, caprolactone, and mixtures of these monomeric repeating units.

Use of the term copolymers is intended to include within the scope of the invention polymers formed of two or more unique monomeric repeating units. Such copolymers can include random copolymers, graft copolymers, block copolymers, radial block, diblock, triblock copolymers, alternating copolymers, and periodic copolymers. Use of the term polymer blend is intended to include polymer alloys, semi-interpenetrating polymer networks (SIPN) and interpenetrating polymer networks (IPN).

Preferred shape-memory molded implants of this invention are fabricated to include homopolymers, copolymers, polymer blends, and oligomers of d, 1, d/l, polylactide; polyglycolide, poly(lactide-co-glycolide), poly($\beta$-hydroxy butyrate); poly($\beta$-hydroxy butyrate-co-hydroxyvalerate), poly(trimethylene carbonate) polyurethane, poly(ethylene-co-vinyl acetate) (EVA), poly(ethylene-co-propylene) (EPR), poly(ethylene-co-propylene-co-diene) a ter-polymer (EPDM), poly($\epsilon$-caprolactone), polyimino carbonates, polyanhydrides, copolymers of ethylene and propylene and/ or other $\alpha$-olefins: or copolymers of these $\alpha$-olefins. Among them, various types of polyethylene, such as low-density polyethylene, linear low-density polyethylene, medium-density polyethylene and high-density polyethylene, and polypropylene are preferable.

Preferred polymers include biodegradable homopolymers of lactide or glycolide or copolymers thereof. Exemplary polymers are described in U.S. Pat. No. 4,950,258, the entire disclosure of which is incorporated by reference herein. When copolymers of lactide and glycolide are used to form the spacers, the copolymers preferably consist essentially of a composition of 90–10 mol. % lactide and 10–90 mol. % glycolide, and most preferably consist essentially of 80–20 mol. % lactide and 20–80 mol. % of glycolide. Within these specified ranges, the copolymers exhibit desirable deformation characteristics. For example, the copolymers are more pliable and readily deformable at lower temperatures when their mole ratio of lactide and glycolide approximates to 1:1. Generally, the less crystalline phases in the SMP material, the lower the deformation temperature.

The polymer composition of the present invention may further contain a thermoplastic resins and/or thermoplastic elastomers to improve its stiffness, moldability, and formability. In addition, the shape-memory spacer may additionally include additives such as coloring agents, stabilizers, fillers and the like, in an amount such as will not alter the desired shape memory effect, biocompatibility and/or biodegradability properties of the molded spacers.

The polymer is characterized in that it will attempt to assume its memory condition by activation of a polymer transition. Activation can occur by adsorption of heat by the polymer, adsorption of liquid by the polymer, or a change in pH in the liquid in contact with the polymer. The polymer is formulated to be responsive to adsorption of a liquid by incorporating in the polymer a hydrophilic material, such an n-vinyl pyrrolidone. Incorporation of a material such as methacrylic acid or acrylic acid into the polymer results in a polymer having a transition that is sensitive to pH. The polymer transition may be a thermally activated transition, where upon adsorption of heat the polymer undergoes a glass transition or a crystalline melting point.

It is also considered to be within the scope of the present invention to provide intervertebral spacers that are formed of a laminate material that comprises one or more layers of a shape memory polymeric material. For example, spacer 10 can be provided with an upper surface 14 that includes an exterior layer of a shape memory polymeric material. Similarly, lower surface 16 can also be provided with a laminated layer of a shape memory polymer. The material used to form the sidewall 16 can be formed of any conventional biocompatible polymeric material. In preferred forms, the peripheral sidewall is formed of a biodegradable polymeric material as has been described above. When thus provided, the laminated spacer can be provided to include a varying compressive modulus, depending upon the deformation of the spacer at a constant temperature. For example, a laminated structure where the external layers are formed of a shape memory polymeric material can have a compressive modulus that is significantly less than the polymeric material used to form the intermediate layer for the peripheral sidewall 114. This provides distinct advantages for spacers by use of the present invention. For example, spacers can have layers varying in compressive strength to allow greater flexibility of the spine. Alternatively, the laminated structure can provide varying rates of biodegradability in the body. For example, the external laminated layers can be provided in a form having less crystallinity than the intermediate layer for the peripheral sidewall. When polymers such as biodegradable polymers are provided with less crystallinity, they degrade at a much faster rate than polymers that have greater degrees of crystallinity. Polymers with less degree of crystallinity can be prepared by providing copolymers of lactic acid and glycolic acid. Increasing the amount of glycolic acid in the polymer decreases its crystallinity and therefore increases its rate of degradation.

As mentioned above, the spacer can be deformed when heated above its deformation temperature. The deformation temperature ($T_d$) in most situations will be substantially equal to the glass transition temperature ($T_g$). When heated above its deformation temperature, the polymeric material exhibits a elasticity or super elasticity that allows it to be molded into a variety of shapes. For example, for the present invention, the molded spacer can be heated to a temperature between about 40° and about 100° C. Application of a compressive force to deform the spacer into a deformed configuration having a reduced cross-sectional profile can then be applied. Preferred examples of the compressive force needed to deform the spacer are in a range between about 18 KPa and about 900 KPa. The deformed spacer can then be cooled below the $T_d$, which effectively freezes the deformed implant into its deformed configuration. The deformed spacer can be used immediately, or the deformed spacer can be stored and/or shipped for use at a later time. Obviously, prior to use the deformed spacer should be sterilized, preferably using chemical or radiation sterilization techniques.

During surgery, the disc space is prepared to receive the deformed implant. The surgical techniques for partial or full discectomy are commonly known by surgeons skilled in the art. The deformed implant can be inserted from a variety of directions, including posteriorly, anteriorly, or posterior laterally.

After implantation of the deformed spacer into the prepared disc space, the deformed spacer is then heated above its glass transition temperature. This can be accomplished by a variety of techniques and instrumentation. For example, the deformed spacer can be flushed with warm saline solution, which can then be suctioned out of the patient. Obviously, it is preferable that the warm saline solution be kept at a low enough temperature that it does not traumatize or damage the adjacent tissue. Alternatively, when the spacer includes an opening into its sidewall, the osteogenic material may be heated sufficiently high and thereafter injected into the opening into the peripheral sidewall of the deformed spacer. This can be done in addition to or instead of flushing the disc space with warm, sterile saline solution.

In yet another embodiment, a heating tool or other suitable electronic device can be used to heat the implanted deformed spacer without warming and traumatizing the adjacent body tissue. Any suitable heat generating apparatus can be used to heat the SMP material such as a hot air gun, a small welding or soldering gun, or an electrocauter tip. Also usable are lasers, which are commonly provided in operating rooms. Lasers are especially desirable because they are precise and controlled in their application, can generate sufficient heat very quickly, and cause less thermal necrosis because there is less misdirected heat. The heating operation can be performed during surgery, in the body. Still other embodiments include the use of ultra sonic devices, light, and/or other electromagnetic radiation generating devices.

After the deformed spacer has been heated above its deformation temperature, the deformed spacer automatically undergoes a transition in which it reverts back to its originally molded configuration. However, as has been discussed above, due to spatial constraints within the disc space, the deformed spacer may not be able to obtain the full height ($H_1$) that was originally provided in the originally molded spacer.

When the expanded spacer has been expanded to the desired height, the surgeon can then remove the heat source, thus allowing the expanded spacer to cool down below the deformation temperature and freeze it into its second or expanded confirmation. The spacers will cool to below their deformation temperature in a relatively short time. After the spacers are frozen into their expanded configuration, the surgeon can reduce any distraction that has been applied to the adjacent vertebral bodies. In this expanded confirmation, the implanted spacer has sufficient compressive modulus to withstand the biomechanical load exerted by the spinal column.

To further increase the compressive modulus of the spacer, the polymeric material used to form the spacer can include a wide variety of additives such as fillers; binders; reinforcement phases, such as fibers, for example, glass fiber and carbon fibers and the like; aggregates, for example, ceramic particles or bone derived particles; and platelets.

The spacer can be fabricated by a wide variety of techniques, including injection molding, extrusion molding, vacuum molding, blow molding, and transfer molding. The laminated structures can be fabricated using techniques known in the art including coextrusion, overmolding of the adjacent layers and using biocompatible adhesives to form the laminated structures.

The term osteogenic material used here means virtually any osteo-conductive or osteo-inductive material that promotes bone growth or healing, including natural, synthetic and recombinant proteins, hormones, and the like. The osteogenic materials used in this invention preferably comprise a therapeutically effective amount of a bone inductive factor such as a bone morphogenic protein in a pharmaceutically acceptable carrier. Examples of factors include recombinant human bone morphogenic proteins (rhBMPs) rhBMP-2, rhBMP-4 and heterodimers thereof. However, any bone morphogenic protein is contemplated, including bone morphogenic proteins designated as BMP-1 through BMP-13, which are available from Genetics Institute, Inc., Cambridge, Mass. All osteoinductive factors are contemplated whether obtained as above or isolated from bone.

The osteogenic material can include a demineralized bone matrix and optionally a carrier, such as a gelatin substance. The demineralized bone matrix can be provided in the form of a powder, paste or gel. When provided as a powder, the osteogenic material can be reconstituted with sterile water, saline, glycerin or other physiological solutions. The reconstituted material is molded about the implant assembly. An osteogenic material can be applied to the intervertebral spacer by the surgeon during surgery or the spacer may be supplied with the composition pre-applied. In such cases, the osteogenic composition may be stabilized for transport and storage. The osteogenic material can be provided as a putty that can be retained in and about the implant assembly. The osteogenic putty is a moldable, flowable material that sets up to a semi-rigid form at about body temperature. The intervertebral spacer with the osteogenic material is then inserted into a prepared disc space. The osteogenic material can also include a reinforcement component such as bone chips, preferably cortical bone chips. Examples of osteogenic material suitable for use with this invention include, but are not limited to: OSTEOFIL, which is commercially available from Regeneration Technologies, Inc. of Alachua, Fla.; GRAFTON CRUNCH available from Osteotech of Eatontown, N.J. and ALLOMATRIX, available from Allosource of Denver, Colo.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An intervertebral spacer for implantation into a disc space between adjacent vertebrae, said spacer comprising a deformable body formed to include a shape memory polymeric material, said body comprising: a first bearing surface, an opposite, second bearing surface and a peripheral sidewall positioned therebetween, said spacer having a lateral axis extending therethrough and positioned to lie substantially parallel said first bearing surface, and wherein said body deforms in a direction along said lateral axis upon application of thermal or photoradiation energy.

2. The spacer of claim 1 wherein the spacer is cylindrical.

3. The spacer of claim 1 wherein the spacer comprises an elongate, body.

4. The spacer of claim 1 wherein the spacer is "C" shaped.

5. The spacer of claim 1 wherein the peripheral sidewall collapses back onto itself.

6. The spacer of claim 1 wherein the peripheral sidewall comprises a first lateral wall portion, an opposite second lateral wall portion, and an end wall portion positioned therebetween.

7. The spacer of claim 1 wherein the body comprises an interior cavity.

8. The spacer of claim 1 wherein the body deforms upon application of photoradiation energy.

9. The spacer of claim 1 wherein the body deforms when heated to a temperature level between about 38° C. and about 100° C.

10. The spacer of claim 9 wherein the body deforms when heated to a temperature level between about 40° C. and about 65° C.

11. The spacer of claim 9 wherein the body at a temperature below the deformation temperature exhibits a compression modulus comparable to that of cortical bone.

12. The spacer of claim 9 wherein the body is adapted to withstand 500 N compressive force without significant deformation when maintained below the deformation temperature.

13. The spacer of claim 1 wherein the body is provided in a first configuration having a first cross-sectional profile positioned orthogonal to said lateral axis, wherein said body deforms to a second configuration having a second cross-sectional profile positioned orthogonal to said lateral axis, said second cross-sectional profile smaller than said first cross-sectional profile.

14. The spacer of claim 1 wherein the polymeric material is biodegradable.

15. The spacer of claim 1 wherein the shape memory polymeric material is selected from the group consisting of: polylactide, polyglycolide, poly(lactide-co-glycolide), polyurethane, poly(ethylene-co-vinyl acetate), poly(ethylene-co-propylene), poly(ethylene-co-propylene-co-diene), poly($\epsilon$-caprolactone), poly($\beta$-hydroxybutyrate), poly($\beta$-hydroxybutyrate-co-hydroxyvalerate), poly(methacrylate), poly(methyl methylacrylate), poly(acrylate), and mixtures, copolymers and blends thereof.

16. The spacer of claim 1 wherein the body is provided in an original configuration.

17. A method of orthopedic treatment, said method comprising:

preparing one or more vertebrae to receive a spacer, implanting a spacer to contact one or more vertebrae, said spacer formed of a material comprising a shape memory polymer and provided in an original configuration and deformable to a second configuration, wherein said spacer reverts to the original configuration by action of the shape memory polymer, and subjecting said spacer to thermal or photoradiation energy wherein said spacer deforms.

18. The method of claim 17 wherein said subjecting comprises subjecting the spacer to thermal or photoradiation energy after the spacer has been implanted.

19. The method of claim 17 comprising heating the spacer to a temperature between about 40° C. and about 65° C.

20. The method of claim 17 wherein the body is cylindrical or C-shaped.

21. The method of claim 17 wherein the body is kidney-shaped.

22. The method of claim 17 wherein the spacer is implanted into a disc space between adjacent vertebrae.

23. The method of claim 17 wherein the body expands laterally in a prepared disc space.

24. The method of claim 17 wherein the body includes an interior cavity for receipt of an osteogenic material.

25. The method of claim 17 wherein the spacer is biodegradable.

26. The method of claim 17 wherein the spacer is implanted into a vertebral body.

* * * * *